(12) United States Patent
Acosta

(10) Patent No.: US 10,557,785 B2
(45) Date of Patent: Feb. 11, 2020

(54) TEST METHOD TO SIMULATE SHALE OIL RECOVERY

(71) Applicant: Alchemy Sciences, Inc., Houston, TX (US)

(72) Inventor: Erick Acosta, Sugar Land, TX (US)

(73) Assignee: ALCHEMY SCIENCES, INC., Houston, TX (US)

( * ) Notice: Subject to any disclaimer, the term of this patent is extended or adjusted under 35 U.S.C. 154(b) by 0 days.

(21) Appl. No.: 16/378,237

(22) Filed: Apr. 8, 2019

(65) Prior Publication Data

US 2019/0317005 A1     Oct. 17, 2019

Related U.S. Application Data

(60) Provisional application No. 62/656,227, filed on Apr. 11, 2018.

(51) Int. Cl.
| | | |
|---|---|---|
| *G01N 15/08* | (2006.01) | |
| *G01N 33/24* | (2006.01) | |
| *E21B 49/00* | (2006.01) | |
| *E21B 41/00* | (2006.01) | |
| *E21B 43/267* | (2006.01) | |

(52) U.S. Cl.
CPC .......... *G01N 15/082* (2013.01); *E21B 41/00* (2013.01); *G01N 15/0806* (2013.01); *E21B 43/267* (2013.01); *E21B 49/00* (2013.01); *G01N 33/24* (2013.01); *G01N 2015/0846* (2013.01)

(58) Field of Classification Search
CPC .......................... G01N 15/082; E21B 43/267
See application file for complete search history.

(56) References Cited

U.S. PATENT DOCUMENTS

| | | | |
|---|---|---|---|
| 3,175,616 A | 3/1965 | Huitt et al. | |
| 4,848,145 A * | 7/1989 | Blaschke | E21B 43/267 |
| | | | 73/152.55 |
| 5,263,360 A * | 11/1993 | Blauch | C09K 8/58 |
| | | | 166/250.02 |
| 5,297,420 A * | 3/1994 | Gilliland | G01N 15/08 |
| | | | 73/38 |
| 6,069,118 A * | 5/2000 | Hinkel | E21B 43/26 |
| | | | 166/308.1 |
| 9,422,470 B2 | 8/2016 | Xu | |
| 2003/0196805 A1 | 10/2003 | Boney et al. | |
| 2009/0029878 A1 * | 1/2009 | Bicerano | C09K 8/035 |
| | | | 507/107 |
| 2009/0306898 A1 | 12/2009 | Anschutz et al. | |
| 2013/0233536 A1 | 9/2013 | Alqam et al. | |
| 2015/0059447 A1 | 3/2015 | Rickards et al. | |
| 2017/0030819 A1 * | 2/2017 | McCarty | G01N 15/082 |
| 2018/0156708 A1 * | 6/2018 | Drake | E21B 43/26 |
| 2019/0226970 A1 * | 7/2019 | Dusterhoft | E21B 49/00 |

OTHER PUBLICATIONS

International Search Report and Written Opinion issued in Application No. PCT/US2019/026373, dated Jun. 25, 2019, 7 pages.

* cited by examiner

*Primary Examiner* — Herbert K Roberts
(74) *Attorney, Agent, or Firm* — Adolph Locklar

(57) ABSTRACT

A fracture simulated oil recovery test apparatus includes a sleeve, the sleeve positioned within an oven and an oil saturated matrix positioned within the sleeve. The fracture simulated oil recovery test apparatus further includes a proppant pack positioned within the oil saturated matrix, the proppant pack having an inlet an outlet and a controller, the controller adapted to control the pressure within the oil saturated matrix.

18 Claims, 3 Drawing Sheets

TEST METHOD TO SIMULATE SHALE OIL RECOVERY

This application is a non-provisional application which claims priority from U.S. provisional application No. 62/656,227, filed Apr. 11, 2018 which is incorporated by reference herein in its entirety.

BACKGROUND

Field

The disclosure relates generally to the field of treatment fluids used in fracturing subterranean formations during hydrocarbon recovery. More specifically the disclosure relates to methods for selecting surfactants used in treatment fluids.

Background Art

Recovery of hydrocarbons from low permeability reservoirs may be difficult. Hydrocarbons in such low permeability reservoirs may be held within a matrix of small pores. The permeability of this matrix may be quite low, often less than one millidarcy. Hydraulic fracturing is a formation stimulation technique used to create additional permeability in a low permeability reservoir to increase the flow of hydrocarbons toward a wellbore. Typically, during a hydraulic fracturing operation, a high hydraulic pressure treatment fluid (referred to herein as a "treatment fluid") is used to fracture the formation, creating hydraulic fractures that facilitate the increased flow of hydrocarbons from the low permeability reservoir. The hydraulic fractures and naturally occurring microfractures, collectively the "fracture network" may then transport the hydrocarbon to the wellbore. Proppants may be used to keep the fracture network open that were created during the fracturing operation.

Treatment fluids include a number of components and are most often water-based. These components typically include acids, biocides, breakers, corrosion inhibitors, friction reducers, gels, iron control chemicals, oxygen scavengers, surfactants and scale inhibitors. The treatment fluid in combination with the hydrocarbon may flow from the matrix to the fracture network. The treatment fluid and hydrocarbons may then flow from the fracture network to the wellbore.

The surfactant in the treatment fluid may act to increase productivity from low permeability reservoirs, such as by enhancing water imbibition into the matrix and aiding oil flow from the fracture network to the wellbore. Selection of a surfactant for the treatment fluid may be determined by a number of factors, including, but not limited to wettability, interfacial surface tension, ability to emulsify, and compatibility with other components of the treatment fluid.

A traditional method for selection of a surfactant includes, for example, an oil recovery test using an oil recovery column, as shown in FIG. 1. FIG. 1 depicts oil recovery column 300, which includes glass column 310. Crushed formation cores 320 are placed within glass column 310. Subsequently, stage two surfactant 330 is poured into glass column 310 above crushed formation core 320. Effluent is collected in sample collectors 340. Oil recovery column 300 and associated testing is described in U.S. Pat. No. 9,422,470 B2. While use of the oil recovery column is a quick screening test that may be performed inexpensively, tests performed using the oil recovery column may not resemble field conditions and use a different mechanism for oil mobilization.

SUMMARY

A fracture simulated oil recovery test apparatus is disclosed. The fracture simulated oil recovery test apparatus includes a sleeve, the sleeve positioned within an oven and an oil saturated matrix positioned within the sleeve. The fracture simulated oil recovery test apparatus further includes a proppant pack positioned within the oil saturated matrix, the proppant pack having an inlet an outlet and a controller, the controller adapted to control the pressure within the oil saturated matrix.

A process for fracture simulated oil recovery is disclosed. The process includes forming an oil saturated matrix, positioning a proppant pack within the oil saturated matrix, and flowing a treatment fluid through the proppant pack. The process also includes maintaining the pressure and temperature of the proppant pack at a temperature and pressure approximating a low permeability reservoir and measuring an effluent from the proppant pack to determine oil recovery.

BRIEF DESCRIPTION OF THE DRAWINGS

The present disclosure is best understood from the following detailed description when read with the accompanying figures. It is emphasized that, in accordance with the stand practice in the industry, various features are not drawn to scale. In fact, the dimensions of the various features may be arbitrarily reduced for clarity of discussion.

DETAILED DESCRIPTION

Figure 1:
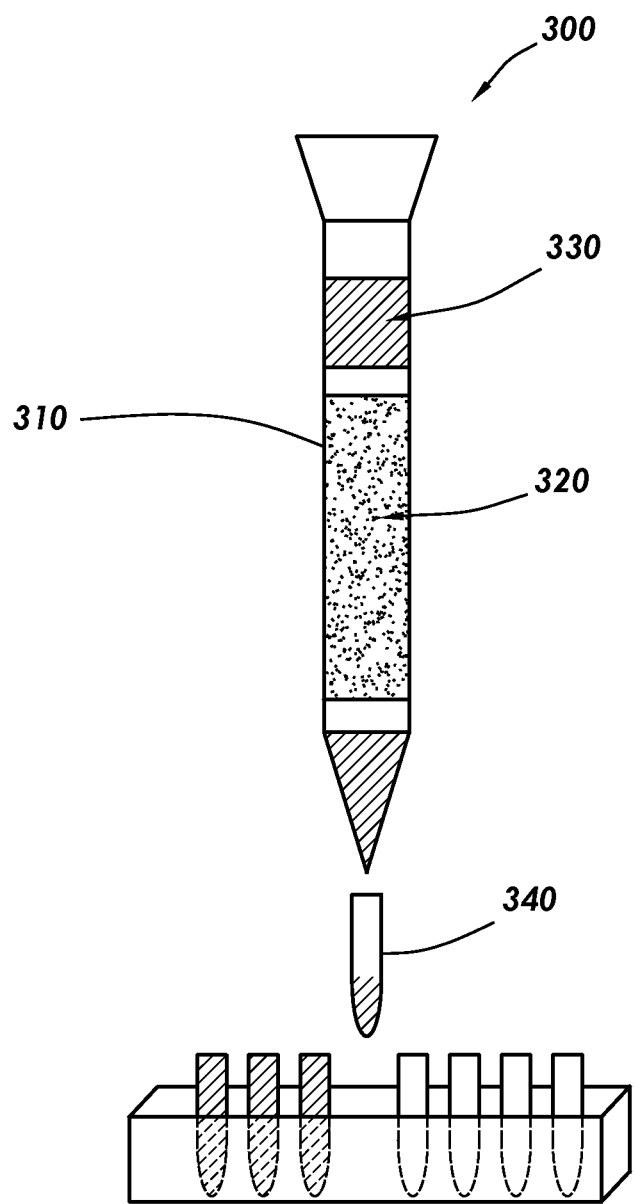
FIG. 1 is a depiction of an oil recovery column for a conventional oil recovery test.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations. For example, if the detailed description recites a range of from 1 to 5, that range includes all iterative ranges within that range including, for instance, 1.3-2.7 or 4.9-4.95.

The present disclosure relates to methods for testing methods for treatment fluids for low permeability reservoirs. As used herein, "low permeability reservoir" is defined to any reservoir having a matrix permeability of less than 500 millidarcies (mD). A non-limiting example of a low permeability reservoir is an oil-containing shale formation. As used herein, "shale" may refer to a fine grain reservoir such as a mudstone, siltstone, or limey mudstone.

Processes in which such treatment fluids may be used may include, but are not limited to, hydraulic fracturing treatments, enhanced oil recovery treatments (including, for instance, water flooding treatments and polymer flooding treatments), acidizing treatments, and drilling. In certain embodiments, the low permeability reservoir may be contacted by the treatment fluid, such as, for instance, introduction into a well bore that penetrates the low permeability reservoir.

Figure 2:
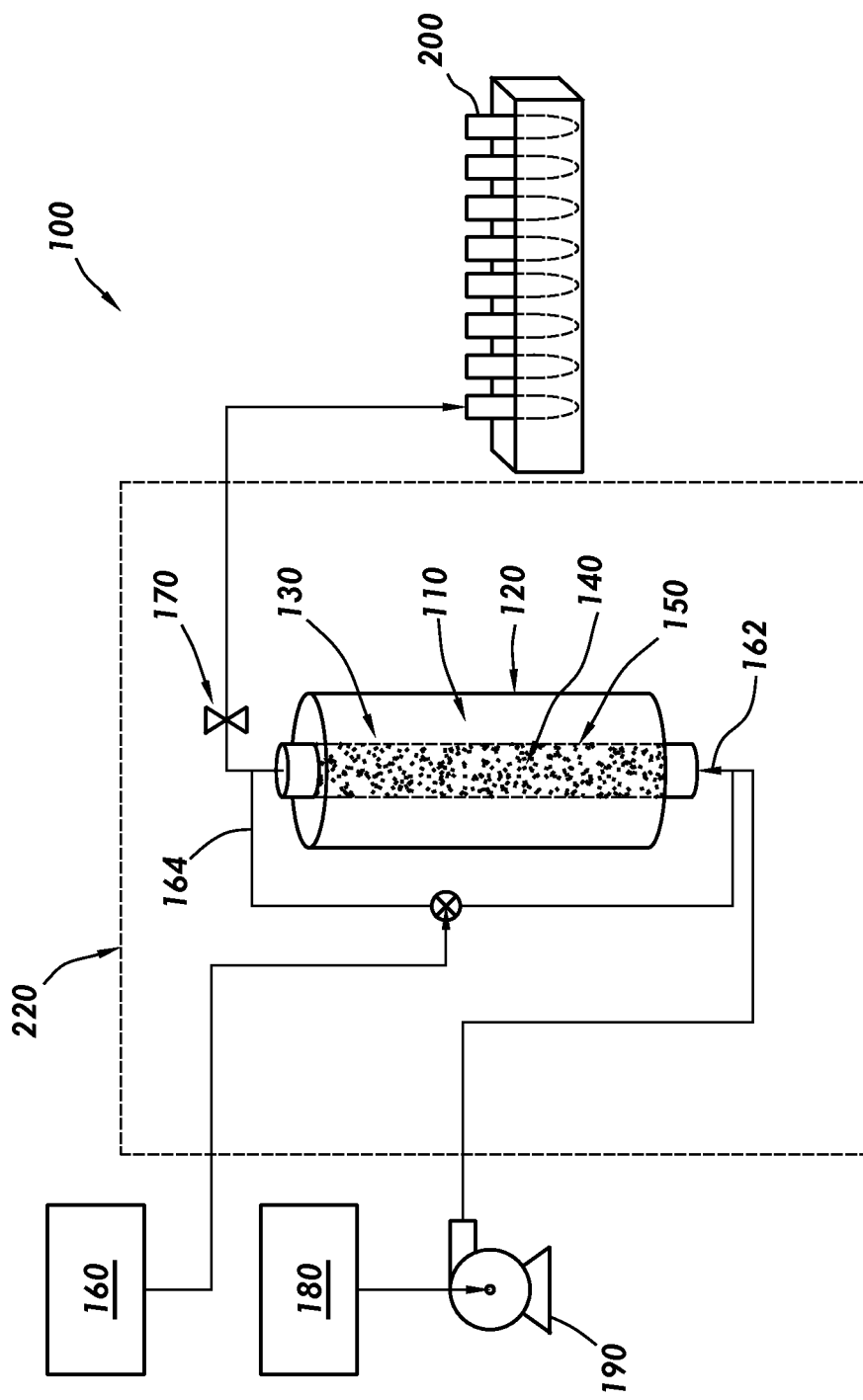
FIG. 2 is a schematic of a fracture simulated oil recovery test apparatus consistent with certain embodiments of the present disclosure.

The present disclosure includes tests and test apparatuses that may be performed to select surfactants for treatment fluids. One such test apparatus is depicted in FIG. 2 as fracture simulated oil recovery test apparatus 100. Fracture simulated oil recovery test apparatus 100 includes oil saturated matrix 110 positioned within sleeve 120. In certain embodiments, sleeve 120 may be an elastomer or other flexible material, such as, for example, a rubber. In other embodiments, sleeve 120 may be an inflexible substance such as metal. In the embodiment shown in FIG. 2, sleeve 120 and oil saturated matrix 110 are cylindrical, although any configuration is contemplated by this disclosure. In certain embodiments, oil saturated matrix 110 is prepared by removing a core sample from the low permeability reservoir, crushing the core sample, and saturating the core sample with oil consistent with oil found in the low permeability reservoir.

Proppant pack 130 is positioned within oil saturated matrix 110. Proppant pack 130 includes proppant 140 surrounded by permeable membrane 150. As shown in FIG. 2, proppant pack 130 is a cylinder positioned coaxially within the cylinder of oil saturated matrix 110. Pressure within sleeve 120 may be adjusted by controller 160. In the embodiment depicted in FIG. 2, pressure of the proppant pack is measured at inlet 162 and outlet 164. Pressure of proppant pack 130 may be adjusted by controller 160 by throttling control valve 170.

As further shown in FIG. 2, treatment fluid reservoir 180 may be in fluid communication with pump 190. In certain embodiments, pump 190 may be a HPLC (high performance liquid chromatograph pump). Pump 190 may be in fluid communication with inlet 162 of proppant pack 130. Outlet 164 of proppant pack 130 may be fluidly connected through control valve 170 to a collection point for effluent from proppant pack 130, shown herein as autosampler 200. In certain embodiments, sleeve 120 and components located therewithin, including, for example, proppant pack 130 and oil saturated matrix 110, may be positioned within oven 220.

In certain embodiments, fracture simulated oil recovery test apparatus may be used to determine the ability of a surfactant within the treatment fluid to penetrate the low permeability formation, the mobilization of oil from the matrix to the fracture network, the impact to proppant pack conductivity, and any increase in oil production from the core sample. The treatment fluid reservoir 180 may be at least partially filled with a treatment fluid to be tested. The treatment fluid to be tested may include a surfactant. A core sample from a low permeability formation may be extracted, crushed, and saturated with oil consistent with oil from the low permeability reservoir. Oil saturated matrix 110 may then be placed within sleeve 120. Proppant pack 130 may be formed by placing proppant consistent with proppant 140 used in the low permeability formation within permeable membrane 150 and inserting proppant pack 130 within oil saturated matrix 110 (that can include crushed cores, crushed cuttings, outcrop or reservoir cores). Sleeve 120 and associated components therewithin may be positioned within oven 220 and oven 220 heated to a temperature that approximates the temperature of the low permeability formation. The treatment fluid may be pumped by pump 190 into proppant pack 130. Pressure of proppant pack 130 may be adjusted by controller 160 by throttling control valve 170 to approximate the pressure of the low permeability reservoir. Effluent from outlet 164 may be collected in autosampler 200 and measured to determine the amount of oil recovered from oil saturated matrix 110. The fracture simulated oil recovery test may be repeated with different treatment fluids containing different surfactants. In certain embodiments, the treatment fluid having the best oil recovery may be selected.

Figure 3:
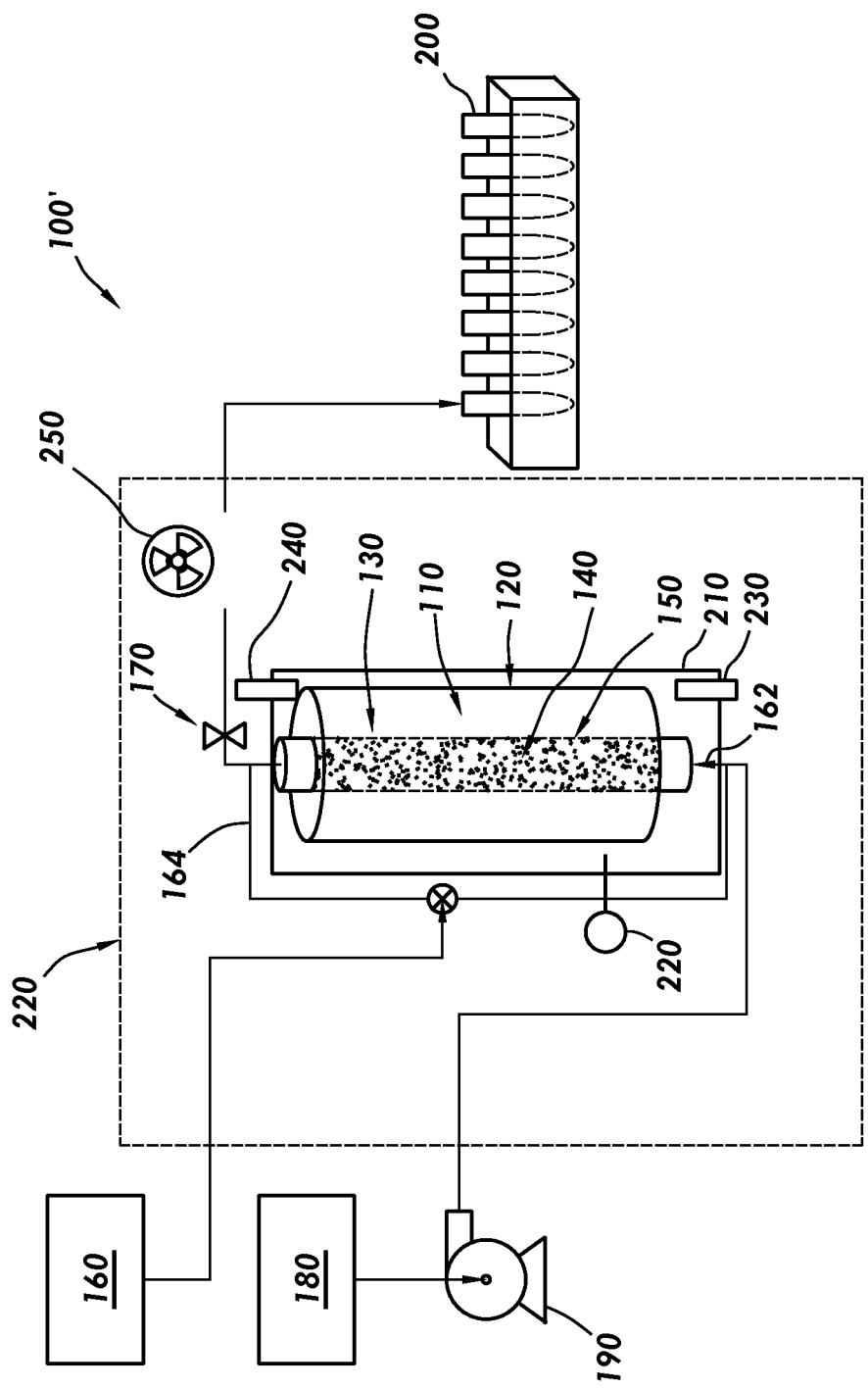
FIG. 3 is a schematic of a fracture simulated oil recovery test apparatus consistent with certain embodiments of the present disclosure

Another embodiment of a test apparatus is depicted in FIG. 3 as fracture simulated oil recovery test apparatus 100'. Fracture simulated oil recovery test apparatus 100' includes high pressure cell 210 disposed around and encompassing sleeve 120. In this embodiment, sleeve 120 is an elastomer or other flexible material. High pressure cell 210 is adapted to hold a higher than atmospheric pressure on proppant pack 130, such as to simulate the pressure present in a formation simulated by simulated oil recovery test apparatus 100'. The pressure in high pressure cell 210 may be controlled by pressure controller 260 by controlling pressure inlet 230 and pressure outlet 240. The high pressure controller may be in signal communication with pressure inlet 230 and pressure outlet 240. By controlling the pressure outside sleeve 120, oil saturated matrix 110 may be subjected to pressure through sleeve 120.

In yet another embodiment, as shown in FIG. 3, CT scanner 250 may be included for imaging oil saturated matrix 110. CT scanner 250 may scan inlet two-phase flow into and out of oil saturated matrix 110, thereby making it possible to evaluate how much oil has left oil saturated matrix 110.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure and that they may make various changes, substitutions, and alterations herein without departing from the spirit and scope of the present disclosure.

What is claimed is:

1. A fracture simulated oil recovery test apparatus comprising:
   a sleeve, the sleeve positioned within an oven;
   an oil saturated matrix positioned within the sleeve;
   a proppant pack positioned within the oil saturated matrix, the proppant pack having an inlet an outlet; and
   a controller, the controller adapted to control the pressure within the oil saturated matrix.

2. The fracture simulated oil recovery test apparatus of claim 1 further comprising:
   a treatment fluid reservoir, the treatment fluid reservoir in fluid communication with the inlet through a pump; and
   a collector, the collector in fluid communication with the outlet through a flow valve.

3. The fracture simulated oil recovery test apparatus of claim 2, wherein the controller is adapted to control the pressure within the oil saturated matrix using the flow valve.

4. The fracture simulated oil recovery test apparatus of claim 2, wherein the collector is an autosampler.

5. The fracture simulated oil recovery test apparatus of claim 1, wherein the proppant pack comprises proppant surrounded by a permeable membrane.

6. The fracture simulated oil recovery test apparatus of claim 1 further comprising a high pressure cell, the high pressure cell disposed around and encompassing the sleeve.

7. The fracture simulated oil recovery test apparatus of claim 6, wherein the sleeve is an elastomer.

8. The fracture simulated oil recovery test apparatus of claim 7, further comprising a pressure controller, the pressure controller in signal communication with a pressure inlet and a pressure outlet, the pressure inlet and pressure outlet disposed on the high pressure cell.

9. The fracture simulated oil recovery test apparatus of claim 1, wherein the soil saturated matrix includes crushed cores, crushed cuttings, outcrop, reservoir cores, or combinations thereof.

10. The fracture simulated oil recovery test apparatus of claim 1 further comprising a CT scanner, the CT scanner adapted for imaging the oil saturated matrix.

11. A process for fracture simulated oil recovery comprising:
   forming an oil saturated matrix;
   positioning the oil saturated matrix within a sleeve;
   positioning a proppant pack within the oil saturated matrix;
   flowing a treatment fluid through the proppant pack;
   maintaining the pressure and temperature of the proppant pack at a temperature and pressure approximating a low permeability reservoir; and
   measuring an effluent from the proppant pack to determine oil recovery.

12. The method of claim 10, wherein the step of forming an oil saturated matrix comprises:
   extracting a crushed core, crushed cutting, outcrop, reservoir core, or combination thereof from the reservoir to be tested;
   and
   saturating the crushed core, crushed cutting, outcrop, reservoir core, or combination thereof with oil.

13. The method of claim 11, wherein the proppant pack is formed by placing a proppant within a low permeability membrane.

14. The method of claim 11, wherein the temperature of the proppant pack is maintained using an oven.

15. The method of claim 11, wherein the pressure of the proppant pack is mainlined by:
   measuring a pressure at an inlet to the proppant pack and an outlet to the proppant pack;
   and
   adjusting pressure using a control valve at the outlet of the proppant pack.

16. The method of claim 15, wherein the control valve is operated with a controller.

17. The method of claim 11 further comprising:
   enclosing the sleeve within a high pressure cell; and
   increasing the pressure within the high pressure cell.

18. The method of claim 11 further comprising imaging the oil saturated matrix with a CT scanner.

* * * * *

UNITED STATES PATENT AND TRADEMARK OFFICE
CERTIFICATE OF CORRECTION

Page 1 of 1

PATENT NO. : 10,557,785 B2
APPLICATION NO. : 16/378237
DATED : February 11, 2020
INVENTOR(S) : Erick Acosta It is certified that error appears in the above-identified patent and that said Letters Patent is hereby corrected as shown below:

In the Specification

In the BRIEF DESCRIPTION OF THE DRAWINGS

Column 2, Line 26:
"stand practice in the industry, various features are not drawn"
Should read:
"standard practice in the industry, various features are not drawn"

In the Claims

Claim 12, Column 6, Line 3:
"The method of claim 10, wherein the step of forming"
Should read:
"The method of claim 11, wherein the step of forming"

Claim 15, Column 6, Line 17:
"proppant pack is mainlined by:"
Should read:
"proppant pack is maintained by:"

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*